United States Patent
Katz et al.

(10) Patent No.: US 10,403,053 B2
(45) Date of Patent: Sep. 3, 2019

(54) MARKING SPARSE AREAS ON MAPS

(71) Applicant: BIOSENSE WEBSTER (ISRAEL) LTD., Yokneam (IL)

(72) Inventors: Natan Sharon Katz, Atlit (IL); Lior Zar, Poria Illit (IL); Benjamin Cohen, Haifa (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 88 days.

(21) Appl. No.: 15/351,972

(22) Filed: Nov. 15, 2016

(65) Prior Publication Data
US 2018/0137687 A1    May 17, 2018

(51) Int. Cl.
*G06T 15/08* (2011.01)
*G06T 19/20* (2011.01)
(Continued)

(52) U.S. Cl.
CPC .............. *G06T 19/20* (2013.01); *A61B 5/044* (2013.01); *A61B 5/0422* (2013.01); *A61B 18/1492* (2013.01); *G06T 7/0014* (2013.01); *G06T 15/08* (2013.01); *G06T 15/80* (2013.01); *G06T 17/20* (2013.01); *G06T 19/00* (2013.01); *A61B 5/06* (2013.01); *A61B 5/6858* (2013.01); *A61B 5/6859* (2013.01); *A61B 2018/00267* (2013.01); *A61B 2018/00351* (2013.01); *A61B 2018/00357* (2013.01); *A61B 2018/00577* (2013.01); *A61B 2018/00791* (2013.01); *A61B 2018/00839* (2013.01); *A61B 2018/00875* (2013.01);
(Continued)

(58) Field of Classification Search
CPC ....... G06T 19/20; G06T 15/08; G06T 7/0014; G06T 15/80; G06T 2207/30048; A61B 5/044
See application file for complete search history.

(56) References Cited

U.S. PATENT DOCUMENTS 5,546,951 A    8/1996 Ben-Haim
6,226,542 B1 *  5/2001 Reisfeld ............. A61B 5/04011
                                                    600/407
(Continued)

FOREIGN PATENT DOCUMENTS

EP         1070480          1/2001
WO    WO 96/05768 A1        2/1996

OTHER PUBLICATIONS

Pending U.S. Appl. No. 14/881,192, filed Oct. 13, 2015.
(Continued)

*Primary Examiner* — Diane M Wills
(74) *Attorney, Agent, or Firm* — Dergosits & Noah LLP; Todd A. Noah

(57) ABSTRACT

Values of a physiologic parameter at respective measured points in a heart are obtained. A 3-dimensional model of the heart is constructed, which includes first spatial elements that include the measured points and second spatial elements that do not include the measured points. The values of the parameter in the second spatial elements are interpolated and regional densities of the measured points in the model determined. The values of the parameter at the first spatial elements and the second spatial elements are displayed on a functional map of the heart, and a graphical characteristic of the map is modified responsively to the regional densities.

9 Claims, 3 Drawing Sheets

(51) Int. Cl.

| | | |
|---|---|---|
| *A61B 5/042* | (2006.01) | |
| *A61B 5/044* | (2006.01) | |
| *A61B 18/14* | (2006.01) | |
| *G06T 7/00* | (2017.01) | |
| *G06T 15/80* | (2011.01) | |
| *G06T 17/20* | (2006.01) | |
| *G06T 19/00* | (2011.01) | |
| *A61B 18/00* | (2006.01) | |
| *A61B 5/00* | (2006.01) | |
| *A61B 5/06* | (2006.01) | |

(52) U.S. Cl.
  CPC ............... *A61B 2018/144* (2013.01); *G06T 2207/30048* (2013.01); *G06T 2210/41* (2013.01)

(56) References Cited

U.S. PATENT DOCUMENTS

| | | |
|---|---|---|
| 6,301,496 B1 | 10/2001 | Reisfeld |
| 6,385,476 B1 | 5/2002 | Osadchy et al. |
| 6,690,963 B2 | 2/2004 | Ben-Haim et al. |
| 6,814,733 B2 | 11/2004 | Schwartz et al. |
| 6,892,091 B1 | 5/2005 | Ben-Haim |
| 6,997,924 B2 | 2/2006 | Schwartz et al. |
| 7,156,816 B2 | 1/2007 | Schwartz et al. |
| 7,536,218 B2 | 5/2009 | Govari et al. |
| 7,756,576 B2 | 7/2010 | Levin |
| 8,478,383 B2 | 7/2013 | Bar-Tal et al. |
| 8,515,521 B2 | 8/2013 | Erdman et al. |
| 2007/0223794 A1 | 9/2007 | Preiss et al. |
| 2007/0299352 A1* | 12/2007 | Harlev ............ A61B 5/0422 600/509 |
| 2009/0262109 A1* | 10/2009 | Markowitz ........ A61B 5/0422 345/419 |
| 2010/0274123 A1 | 10/2010 | Voth |
| 2011/0306896 A1 | 12/2011 | Altmann |
| 2013/0004044 A1 | 1/2013 | Ross et al. |
| 2013/0265302 A1* | 10/2013 | Olivan Bescos ...... G06T 15/08 345/419 |
| 2015/0045647 A1 | 2/2015 | Katz |
| 2016/0171731 A1* | 6/2016 | Kandogan ............ G09G 5/377 345/629 |

OTHER PUBLICATIONS

Pending U.S. Appl. No. 15/009,285, filed Jan. 28, 2016.
Pending U.S. Appl. No. 15/086,220, filed Mar. 31, 2016.
European Search Report for European Application No. 17201534.9, dated Mar. 19, 2018.

* cited by examiner

MARKING SPARSE AREAS ON MAPS

COPYRIGHT NOTICE

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

1. Field of the Invention

This invention relates to image data processing. More particularly, this invention relates to geometrically modeling objects for diagnosis by means of electric currents or magnetic fields.

2. Description of the Related Art 3-dimensional functional images of internal organs are useful in many catheter-based diagnostic and therapeutic applications, and real-time imaging is widely used during surgical procedures. For example, a map of a chamber of the heart may be a 3-dimensional map of the chamber surface, upon which is overlaid a color representative of a parameter of the surface, such as a local activation time (LAT) of the surface.

Mapping of electrical potentials in the heart is now commonly performed, using cardiac catheters comprising electrophysiological sensors for mapping the electrical activity of the heart. Typically, time-varying electrical potentials in the endocardium are sensed and recorded as a function of position inside the heart, and then used to map a local electrogram or local activation time. Activation time differs from point to point in the endocardium due to the time required for conduction of electrical impulses through the heart muscle. The direction of this electrical conduction at any point in the heart is conventionally represented by an activation vector, also referred to herein as a conduction velocity vector, which is normal to an isoelectric activation front, both of which may be derived from a map of activation times. The rate of propagation of the activation front through any point in the endocardium may be represented as a conduction velocity vector.

Localized defects in the heart's conduction of activation signals may be identified by observing phenomena such as multiple activation fronts, abnormal concentrations of activation vectors, or changes in the velocity vector or deviation of the vector from normal values. Examples of such defects include reentrant areas, which may be associated with signal patterns known as complex fractionated electrograms. Once a defect is located by such mapping, it may be ablated if it is functioning abnormally or otherwise treated to restore the normal function of the heart insofar as is possible.

Commonly assigned U.S. Pat. Nos. 5,546,951 and 6,690,963, both issued to Ben Haim, and PCT application WO 96/05768, all of which are incorporated herein by reference, disclose methods for sensing an electrical property of heart tissue, for example, local activation time, as a function of the precise location within the heart. Data are acquired with one or more catheters having electrical and location sensors in their distal tips, which are advanced into the heart. Methods of creating a map of the electrical activity of the heart based on these data are disclosed in commonly assigned U.S. Pat. Nos. 6,226,542 and 6,301,496, both issued to Reisfeld, which are incorporated herein by reference.

Location and electrical activity are typically initially measured on the order of 100 to 200 points on the interior surface of the heart. The generated map, which can be represented as a mesh constructed from the points, may then serve as the basis for deciding on a therapeutic course of action, for example, tissue ablation, to alter the propagation of the heart's electrical activity and to restore normal heart rhythm.

The anatomical mesh provided by a multielectrode catheter is relatively coarse-grained for purposes of display in at least some regions. Therefore, 3-dimensional mapping systems, such as the CARTO® 3 System, available from Biosense Webster, Inc., 3333 Diamond Canyon Road, Diamond Bar, Calif. 91765, have interpolated between measured points.

SUMMARY OF THE INVENTION

For regions on a 3-dimensional map with many measured points the interpolation may be assumed to be reliable, while for regions with relatively few measured points the interpolation may be assumed to be less reliable. One way for the physician to estimate the quality of the interpolation is to display the measured points, but this is unsatisfactory because of visual overload from other information incorporated into the map (e.g., catheter icons).

Embodiments of the invention do not rely on displaying the measured points to measure interpolation quality, Rather, spatial elements of a 3-dimensional model that include the surface, such as voxels, are considered, and the number of measured points within a predetermined Euclidean or geodesic distance of each spatial element counted. If the number of measured points is below a predetermined threshold, a region is assumed to be in a "sparse" zone. If the number is above the threshold, the surface region is not in such a zone. Sparse zones are distinguished by adding shading or other features to a graphical display of the 3-dimensional model.

There is provided according to embodiments of the invention a method, which is carried out by obtaining values of a physiologic parameter at respective measured points in a heart and constructing a 3-dimensional model of the heart that includes including first spatial elements that include the measured points and second spatial elements that do not include the measured points. The method is further carried out by interpolating the values of the parameter in the second spatial elements, determining regional densities of the measured points in the model, displaying the values of the parameter at the first spatial elements and the second spatial elements on a functional map of the heart, and modifying a graphical characteristic of the map responsively to the regional densities.

According to one aspect of the method, the first spatial elements and the second spatial elements are voxels.

According to a further aspect of the method, determining regional densities includes counting the measured points within respective predefined distances from the spatial elements.

According to yet another aspect of the method, determining regional densities includes establishing a binary classification according to whether a count of the measured points therein exceeds or fails to exceed a predefined threshold.

According to an additional aspect of the method, determining regional densities includes clustering spatial elements wherein respective counts of the measured points fail to exceed the predefined threshold.

According to still another aspect of the method, modifying a graphical characteristic includes changing a shading of portions of the map.

There is further provided according to embodiments of the invention an apparatus including electrical circuitry connected to a probe that has at least one sensor on a distal portion thereof. The electrical circuitry is configured for obtaining values of a physiologic parameter at respective measured points in a heart from readings of the at least one sensor. The apparatus includes a memory for storing the values, a display, and a processor connected to the memory. The processor is operative for constructing a 3-dimensional model of the heart, wherein the model includes first spatial elements that include the measured points and second spatial elements that do not include the measured points. The processor is operative for interpolating the values of the parameter in the second spatial elements, determining regional densities of the measured points in the model, presenting the values of the parameter at the first spatial elements and the second spatial elements on a functional map of the heart on the display, and modifying a graphical characteristic of the map responsively to the regional densities.

According to an aspect of the apparatus, the at least one sensor is an electrode and the parameter is a local activation time.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

Overview.

Figure 1:
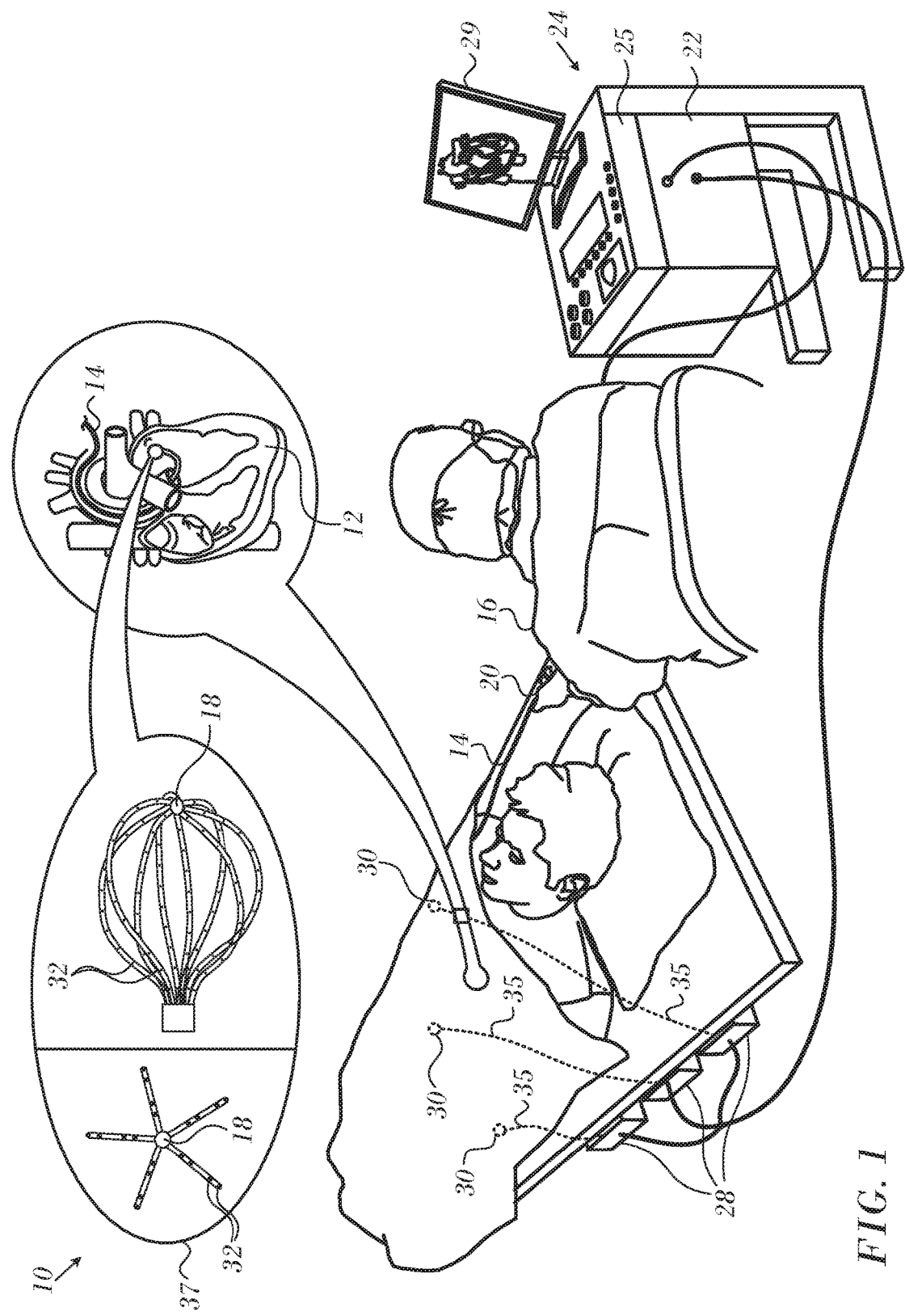
FIG. 1 is a pictorial illustration of a system for evaluating electrical activity in a heart of a living subject in accordance with an embodiment of the invention.

Turning now to the drawings, reference is initially made to FIG. 1, which is a pictorial illustration of a system 10 for evaluating electrical activity in a heart of a living subject, which is constructed and operative in accordance with a disclosed embodiment of the invention. The system comprises a catheter 14, which is percutaneously inserted by an operator 16 through the patient's vascular system into a chamber or vascular structure of a heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference.

The system 10 may comprise a general purpose or embedded computer processor, which is programmed with suitable software for carrying out the functions described hereinbelow. Thus, although portions of the system 10 shown in other drawing figures herein are shown as comprising a number of separate functional blocks, these blocks are not necessarily separate physical entities, but rather may represent, for example, different computing tasks or data objects stored in a memory that is accessible to the processor. These tasks may be carried out in software running on a single processor, or on multiple processors. The software may be provided to the processor or processors on tangible non-transitory media, such as CD-ROM or non-volatile memory. Alternatively or additionally, the system 10 may comprise a digital signal processor or hard-wired logic. One commercial product embodying elements of the system 10 is available as the above-noted CARTO 3 System. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

The catheter 14 is a multi-electrode catheter, which can be a basket catheter as shown in the right portion of balloon 37, or a spline catheter as shown in the left portion. In any case there are multiple electrodes 32, which are used as sensing electrodes and have known locations on the basket or spline, and known relationships to one another. Thus, once the catheter is located in the heart, for example by constructing a current position map, the location of each of the electrodes 32 in the heart is known. One method for generation of a current position map is described in commonly assigned U.S. Pat. No. 8,478,383 to Bar-Tal et al., which is herein incorporated by reference.

Electrical signals can be conveyed to and from the heart 12 from the electrodes 32 located at or near the distal tip 18 of the catheter 14 via cable 34 to the console 24. Pacing signals and other control signals may be conveyed from the console 24 through the cable 34 and the electrodes 32 to the heart 12.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A sensor for obtaining a physiological parameter, such as an electrode or temperature sensor (not shown), typically a thermocouple or thermistor, may be mounted near the distal tip 18 of the catheter 14.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. A suitable positioning subsystem is described in U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the above-noted sensors and a plurality of location sensing electrodes (not shown) located distally in the catheter 14. The digitized signals are received and used by the console 24 and the positioning system to compute the position and orientation of the catheter 14 and to analyze the electrical signals from the electrodes as described in further detail below.

Typically, the system 10 includes other elements, which are not shown in the figures for the sake of simplicity. For example, the system 10 may include an electrocardiogram (ECG) monitor, coupled to receive signals from one or more body surface electrodes, to provide an ECG synchronization signal to the console 24. As mentioned above, the system 10 typically also includes a reference position sensor, either on an externally applied reference patch attached to the exterior of the subject's body, or on an internally-placed catheter, which is inserted into the heart 12 and maintained in a fixed position relative to the heart 12. The system 10 may receive image data from an external imaging modality, such as an MRI unit or the like and includes image processors that can be incorporated in or invoked by the processor 22 for generating and displaying images that are described below. Interpolation.

Continuing to refer to FIG. 1, the principles of the invention are discussed with respect to electrical activation waves in the heart. However, these principles are applicable, mutatis mutandis, to other indicia relating to cardiac physiology, and indeed to other organ systems. In the case of activation waves a functional map is presented to the operator in which the activation time values at particular points in the cardiac chambers are measured by readings from electrodes of the electrodes 32 and presented on the map.

The above-noted Carto System identifies the measured points using location sensors. It has interpolated values between measured points by using a weighted mean that is configured to be inversely proportional to the geodesic distance between points on the surface and has displayed the results in pseudo-colored maps.

Other interpolation techniques facilitate treatment of cases in which the signal lacks an abrupt amplitude jump as a "fuzzy LAT". These interpolation techniques are described in commonly assigned application Ser. No. 15/086,220, entitled Mapping of Atrial Fibrillation, which is herein incorporated by reference.

Commonly assigned U.S. application Ser. No. 14/881,192, entitled Voxelization of a Mesh, which is herein incorporated by reference, interpolates data by first transforming a mesh of triangles into a grid of congruent cubic voxels. Briefly, measured points are interpolated by defining a mesh of a surface, each 3-dimensional triangle in the group having 3-dimensional vertices with respective 3-dimensional coordinates, and transforming each 3-dimensional triangle into a 2-dimensional triangle having 2-dimensional vertices corresponding respectively to the 3-dimensional vertices. Each 2-dimensional vertex has 2-dimensional pixel coordinates and a triplet of pixel attributes corresponding to the 3-dimensional coordinates of a corresponding 3-dimensional vertex. Each 2-dimensional triangle is passed to a graphics processor, which treats the triplet of pixel attributes of each 2-dimensional vertex as interpolatable values. The graphics processor computes respective triplets of interpolated pixel attributes for pixels within each 2-dimensional triangle by interpolation between the pixel attributes of the 2-dimensional vertices, and a 3-dimensional image of the surface is rendered by converting the interpolated pixel attributes computed by the graphics processor into voxel coordinates in the 3-dimensional image.

The voxel interpolation described in the above-noted U.S. application Ser. No. 14/881,192 can be modified using the teachings of commonly assigned application Ser. No. 15/009,285 entitled High Definition Coloring of Heart Chambers, which is herein incorporated by reference. It has been observed that Laplace's equation, $\nabla^2 y = 0$, may be regarded as the perfect interpolator because it minimizes the integrated square of the gradient. This Application describes techniques that deal with certain difficulties in the practical use of Laplacian interpolation. Briefly, a mesh of triangles constructed from measured points obtained from the locations of the electrodes 32 are converted into a grid of congruent cubic voxels. An iterative procedure employing 3-dimensional Laplacian interpolation is applied to a voxel to interpolate the colors representing the interpolated pixel attributes, taking into consideration neighboring voxels. A 3-dimensional image of the voxels is then rendered.

In all of these interpolations, the operator is interested to know the quality (or "goodness") of the interpolation. For regions with many measured points the interpolation may be assumed to be good, while for regions with few points the interpolation may be assumed to be bad. One way to estimate the quality is to display the measured points. However, this is unsatisfactory because there is typically much other information incorporated into the map (e.g., catheter icons), so that judging the sparsity or density of the measured points is difficult due to visual information overload.

In the discussion that follows, spatial elements in a 3-dimensional model are sometimes referred to as voxels. However it will be understood that the principles of the invention are equally applicable to other 3-dimensional volumetric structures known in the art, such as various polygons, spheres, or 4-dimensional doxels. Moreover, in some embodiments the dimensions of a spatial element may be no larger than the height and width dimensions at the graphical resolution of a display monitor for the map, i.e., the dimensions of a 2-dimensional pixel. According to one embodiment of the invention, for each spatial element of the map, the density of measured points near that spatial element is calculated and indicated on the map by a visual scheme, such as shading.

Figure 2:
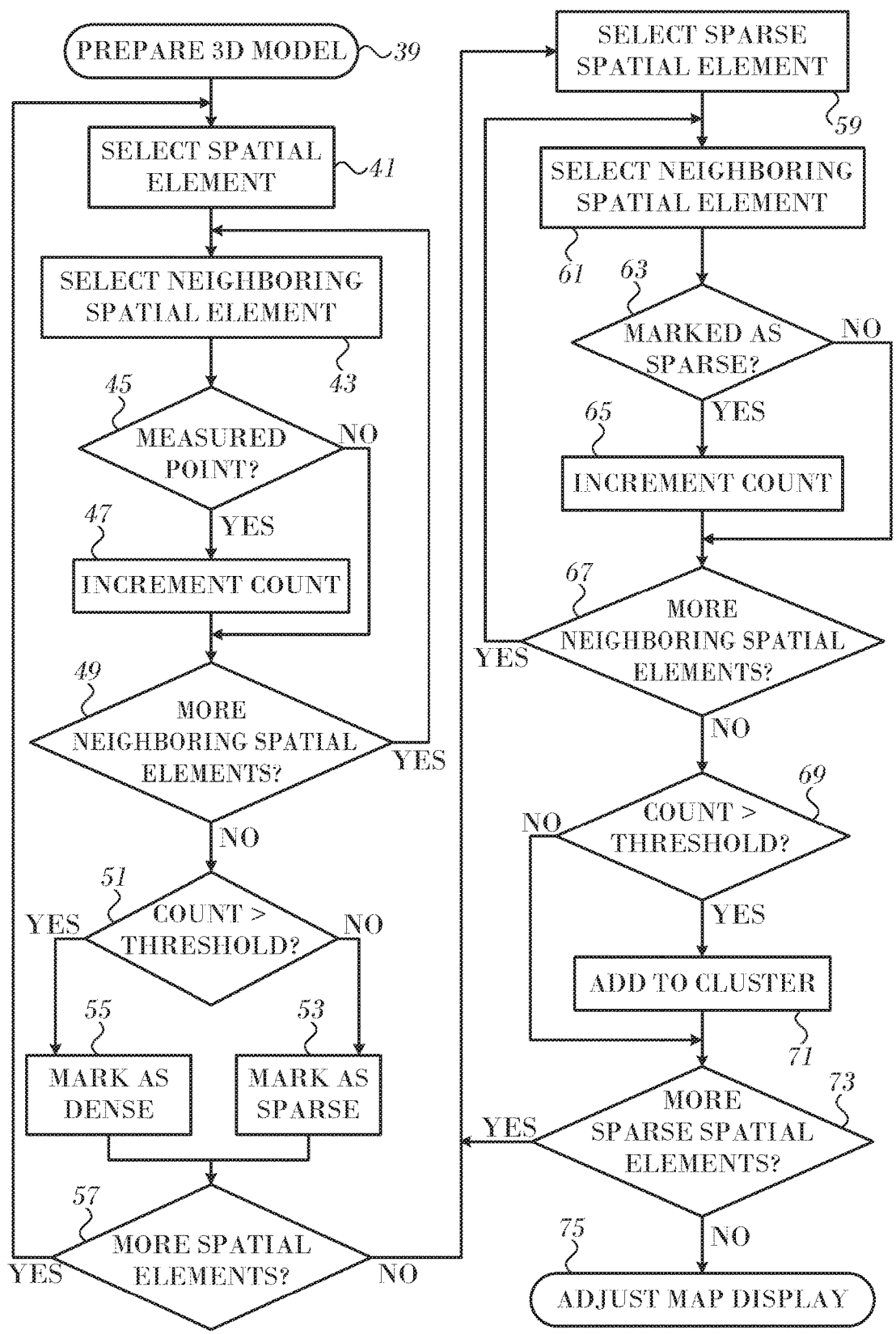
FIG. 2 is a flow chart of a method for displaying the quality of an interpolated map in accordance with an embodiment of the invention.

Reference is now made to FIG. 2, which is a flow chart of a method for displaying the quality of an interpolated map in accordance with an embodiment of the invention. The process steps are shown in a particular linear sequence for clarity of presentation. However, it will be evident that many of them can be performed in parallel, asynchronously, or in different orders. Those skilled in the art will also appreciate that a process could alternatively be represented as a number of interrelated states or events, e.g., in a state diagram. Moreover, not all illustrated process steps may be required to implement the method.

At initial step 39 the heart is catheterized conventionally, typically with a multi-electrode mapping catheter and a 3-dimensional model prepared. A suitable 3-dimensional model for this purpose is a triangular mesh. Values of data in the spatial elements, e.g., voxels that lie between the measured points are interpolated by any of the above-described methods or other suitable interpolation techniques. In the following steps of the procedure, the spatial elements of the model that include the surface of the heart are individually characterized as being within a dense or sparse area of measured points. A functional map, such as an LAT map is prepared from the model, The LAT values on such a map may be displayed in pseudocolors, and the sparse and dense zones graphically distinguished.

Next, at step 41 a current spatial element of the model that includes the surface of the heart is chosen. The current spatial element may include a measured point, but because the process iterates over the map, the current spatial element generally does not include a measured point. A count of measured points in a domain about the current spatial element is set to zero.

Next, at step 43 a neighboring spatial element is selected. Neighboring spatial elements are those spatial elements that include the surface of the heart and lie within a geodesic or Euclidean distance, typically 3-7 mm, from the current spatial element. In other words, neighboring spatial elements lie within a domain comprising a geodesic or Euclidean sphere centered on the geometric center of the current spatial element and having a predetermined radius.

Next, at decision step 45, it is determined if the neighboring spatial element that was selected in step 43 includes a measured point. If the determination at decision step 45 is affirmative, then control proceeds to step 47. The count of measured points is incremented.

After performing step 47 or if the determination at decision step 45 is negative then at decision step 49 it is determined if more neighboring spatial elements remain to be processed. If the determination at decision step 49 is affirmative, then control returns to step 43 to continue iterating over the neighbors of the current spatial element.

If the determination at decision step 49 is negative, then all the neighboring spatial elements in the domain of the current spatial element have been evaluated. At decision step 51, the value of the count of measured points is noted. In the embodiment of FIG. 2 the evaluation comprises a binary decision. It is determined if the count exceeds a predetermined threshold. A value of 2-5 for the count has been found to be satisfactory.

If the determination at decision step 51 is negative, then at step 53 the current spatial element is marked as "sparse" in terms of neighboring measured points, and consequently the quality of the interpolations in the region is potentially poor, subject to a clustering analysis, which follows below.

If the determination at decision step 51 is affirmative, then at step 55 the current spatial element is marked as "dense" in terms of neighboring measured points, and consequently the quality of the interpolations in the region is potentially good, again subject to the clustering analysis. For convenience the regions marked in steps 53, 55 are referred to as "sparse spatial elements" and "dense spatial elements", respectively.

After performing one of steps 53, 55 at decision step 57, it is determined if more spatial elements of the model remain to be evaluated. If the determination at decision step 57 is affirmative, then control returns to step 41 to begin a new iteration.

If the determination at decision step 57 is negative then this phase of the procedure ends. In the next phase clusters of sparse spatial elements, referred to as "sparse clusters" are defined. It will also be apparent to those skilled in the art that when multilevel decisional logic is used, clusters having several densities of measured points can be defined. Control now proceeds to step 59. A sparse spatial element is selected.

Next, at step 61 a neighboring spatial element is selected as described with respect to step 41.

Next, at decision step 63, it is determined if the neighboring spatial element selected in step 61 has been marked as sparse. If the determination at decision step 63 is affirmative, then control proceeds to step 65, where a count is incremented.

After performing step 65 or if the determination at decision step 63 is negative, control proceeds at decision step 67, where it is determined if there are more neighboring spatial elements to be evaluated. If the determination at decision step 67 is affirmative, then control returns to step 61.

If the determination at decision step 67 is negative, then at decision step 69, it is determined if the count that was incremented in step 65 exceeds a threshold value m, meaning that surrounding the currently selected spatial element are at least m sparse spatial elements. Values of the threshold value m in a range of 1-2 are satisfactory.

If the determination at decision step 69 is affirmative, then control proceeds to step 71. The currently selected spatial element is added to a cluster representing a sparsely populated area in terms of measured points. This type of cluster is referred to as a "sparse cluster".

After performing step 71 or if the determination at decision step 69 is negative at decision step 73, it is determined if there are more sparse spatial elements to be evaluated. If the determination at decision step 73 is affirmative, then control returns to step 59 to begin a new iteration.

If the determination at decision step 73 is negative, then control proceeds to final step 75. The portions of the map corresponding to the sparse clusters are modified, e.g., by shading or by a distinctive line pattern, and presented to the operator.

The granularity of the interpolation quality display can be increased by changing the binary decision in decision step 51 and the following details to accommodate multilevel decision logic. The details are within the capabilities of those skilled in the art and are therefore not elaborated here.

Example

Figure 3:
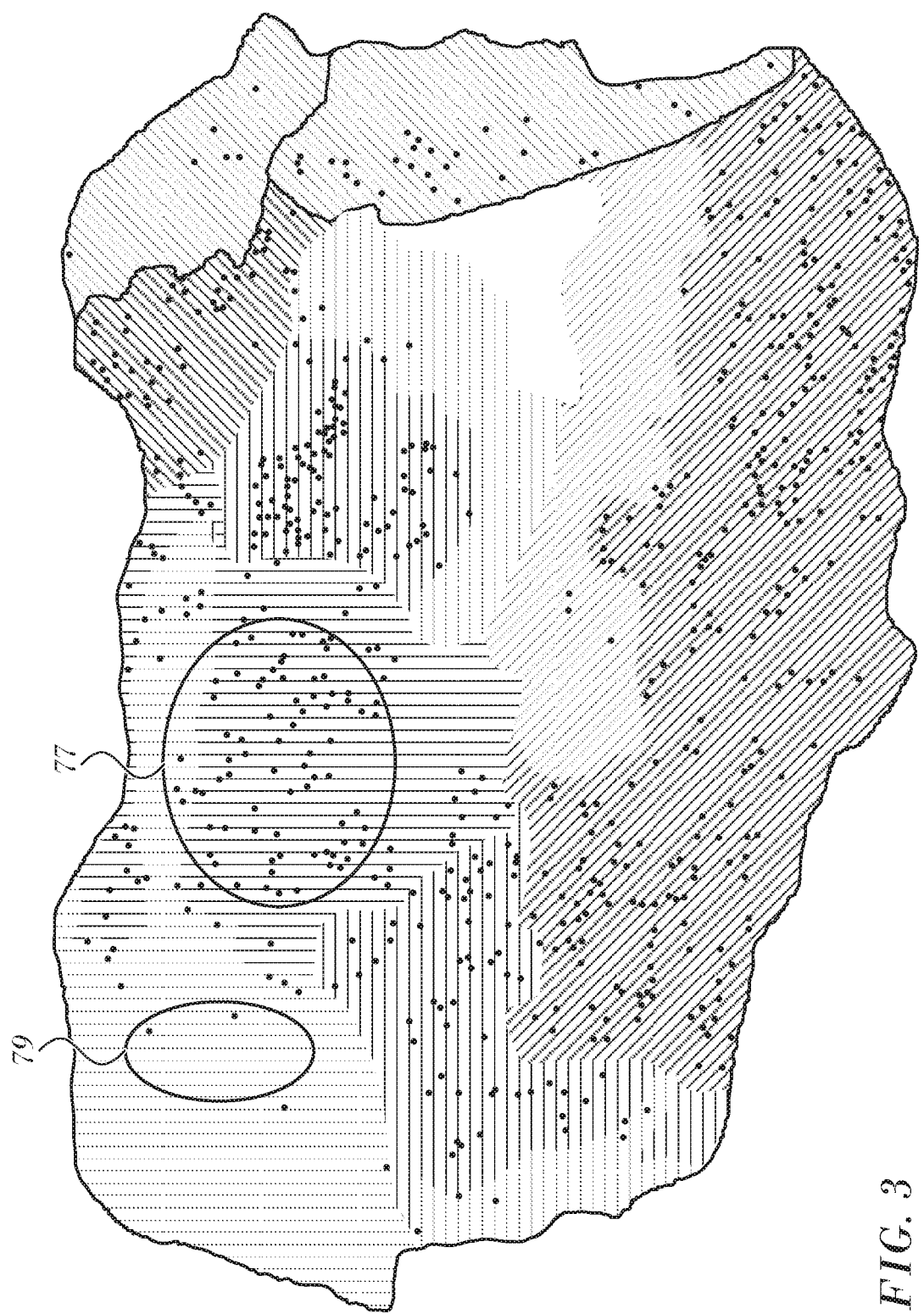
FIG. 3 is an LAT map of the heart, which is prepared in accordance with an embodiment of the invention.

Reference is now made to FIG. 3, which is an LAT map of the heart, which is prepared in accordance with an embodiment of the invention. Measured points are indicated by dots. However, as mentioned above, the display of the measured points on such maps is optional. In region 77 measured points are relatively plentiful in an area indicated by bold hatching, while in region 79 there are fewer measured points. This is indicated by de-emphasizing the intensity of the hatching lines in the region 79. The same effects in hatching are seen in several other areas of the map according to whether the dots in those areas are plentiful or sparse.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
obtaining values of a physiologic parameter at respective measured points in a heart;
constructing a 3-dimensional model of the heart, the model comprising spatial elements including first spatial elements that include the measured points and second spatial elements that do not include the measured points;
interpolating the values of the parameter in the second spatial elements;
determining regional densities of the measured points in the model, the determination comprising comparing a select spatial element to a neighboring spatial element and establishing a binary classification according to whether a count of the measured points in the neighboring spatial element exceeds or fails to exceed a predefined threshold and clustering spatial elements where respective counts of the measured points fail to exceed the predefined threshold;
displaying the values of the parameter at the first spatial elements and the second spatial elements on a functional map of the heart; and
modifying a graphical characteristic of the map responsively to the regional densities.

2. The method according to claim 1, wherein the first spatial elements and the second spatial elements are voxels.

3. The method according to claim 1, wherein determining regional densities comprises counting the measured points within respective predefined distances from the spatial elements.

4. The method according to claim 1, wherein modifying a graphical characteristic comprises changing a shading of portions of the map.

5. An apparatus comprising:
electrical circuitry connected to a probe having at least one sensor on a distal portion thereof, the electrical circuitry configured for obtaining values of a physiologic parameter at respective measured points in a heart from readings of the at least one sensor;
a memory for storing the values;
a display; and
a processor connected to the memory and operative for performing the steps of:
constructing a 3-dimensional model of the heart, the model comprising spatial elements including first spatial elements that include the measured points and second spatial elements that do not include the measured points;
interpolating the values of the parameter in the second spatial elements;
determining regional densities of the measured points in the model, the determination comprising comparing a select spatial element with a neighboring spatial element and establishing a binary classification according to whether a count of the measured points in the neighboring spatial element exceeds or fails to exceed a predefined threshold and clustering spatial elements where respective counts of the measured points fail to exceed the predefined threshold;
presenting, on the display, the values of the parameter at the first spatial elements and the second spatial elements on a functional map of the heart; and
modifying a graphical characteristic of the map responsively to the regional densities.

6. The apparatus according to claim 5, wherein the first spatial elements and the second spatial elements are voxels.

7. The apparatus according to claim 5, wherein determining regional densities comprises counting the measured points within respective predefined distances from the spatial elements.

8. The apparatus according to claim 5, wherein modifying a graphical characteristic comprises changing a shading of portions of the map.

9. The apparatus according to claim 5, wherein the at least one sensor is an electrode and the parameter is a local activation time.

* * * * *